US010793669B2

(12) United States Patent
Le et al.

(10) Patent No.: US 10,793,669 B2
(45) Date of Patent: *Oct. 6, 2020

(54) PROCESS FOR PRODUCING POLYETHER KETONE KETONE

(71) Applicant: ARKEMA FRANCE, Colombes (FR)

(72) Inventors: Guillaume Le, Hérouville-Saint-Clair (FR); Julien Jouanneau, Corneville-sur-Risle (FR)

(73) Assignee: ARKEMA FRANCE, Colombes (FR)

( * ) Notice: Subject to any disclaimer, the term of this patent is extended or adjusted under 35 U.S.C. 154(b) by 134 days.

This patent is subject to a terminal disclaimer.

(21) Appl. No.: 16/053,927

(22) Filed: Aug. 3, 2018

(65) Prior Publication Data

US 2019/0040189 A1  Feb. 7, 2019

(30) Foreign Application Priority Data

Aug. 4, 2017 (EP) .................................... 17306045

(51) Int. Cl.
| | |
|---|---|
| *C07C 45/46* | (2006.01) |
| *C07C 49/784* | (2006.01) |
| *C08G 61/12* | (2006.01) |
| *C08G 65/00* | (2006.01) |
| *C08K 3/16* | (2006.01) |

(52) U.S. Cl.
CPC ............ *C08G 61/127* (2013.01); *C07C 45/46* (2013.01); *C07C 49/784* (2013.01); *C08G 65/00* (2013.01);
(Continued)

(58) Field of Classification Search
CPC .................................................... C08G 61/127
(Continued)

(56) References Cited

U.S. PATENT DOCUMENTS

| | | |
|---|---|---|
| 3,767,620 A | 10/1973 | Angelo et al. |
| 4,698,393 A | 10/1987 | Jansons et al. |

(Continued)

FOREIGN PATENT DOCUMENTS

| | | |
|---|---|---|
| EP | 0 501 436 A2 | 9/1992 |
| WO | 95/23821 A1 | 9/1995 |
| WO | 2011/004164 A2 | 1/2011 |

OTHER PUBLICATIONS

U.S. Appl. No. 15/982,625 claims (Year: 2018).*
(Continued)

*Primary Examiner* — Duc Truong
(74) *Attorney, Agent, or Firm* — Buchanan Ingersoll & Rooney P.C.

(57) ABSTRACT

A method for the manufacture of polyether ketone ketone (PEKK), including:
(i) providing a 1,4-bis(4-phenoxybenzoyl)benzene-Lewis acid complex;
(ii) purifying said 1,4-bis(4-phenoxybenzoyl)benzene-Lewis acid complex;
(iii) reacting said 1,4-bis(4-phenoxybenzoyl)benzene-Lewis acid complex with at least one difunctional aromatic acyl chloride in a reaction solvent and optional additional Lewis acid to obtain a product mixture including a PEKK-Lewis acid complex; and
(iv) decomplexing the PEKK-Lewis acid complex to obtain a PEKK polymer.
Further, a composition including at least 40 wt. % of 1,4-bis(4-phenoxybenzoyl)benzene-Lewis acid complex and an anhydrous aprotic solvent or solvent mixture, characterized in that it includes less than 1 wt. %, preferably less than 0.5 wt. % and in particular less than 0.1 wt. % of molecules including xanthydrol groups and its use for the manufacture of polyether ketone ketone.

17 Claims, 2 Drawing Sheets

(52) U.S. Cl.
CPC ........ *C08K 3/16* (2013.01); *C08G 2261/3442* (2013.01); *C08G 2261/375* (2013.01); *C08G 2261/45* (2013.01); *C08G 2261/712* (2013.01); *C08G 2650/40* (2013.01); *C08K 2003/164* (2013.01)

(58) Field of Classification Search
USPC ........................................................ 528/220
See application file for complete search history.

(56) References Cited

U.S. PATENT DOCUMENTS

| | | |
|---|---|---|
| 4,716,211 A | 12/1987 | Clendinning et al. |
| 4,816,556 A | 3/1989 | Gay et al. |
| 4,841,013 A | 6/1989 | Towle |
| 4,912,181 A | 3/1990 | Becker et al. |
| 4,918,237 A | 4/1990 | Corbin et al. |
| 10,344,125 B2 * | 7/2019 | Le ........................ C07C 7/14891 |
| 10,428,002 B2 * | 10/2019 | Jouanneau ........... C08G 61/127 |
| 10,611,715 B2 * | 4/2020 | Jouanneau .............. C07C 45/46 |

OTHER PUBLICATIONS

U.S. Appl. No. 16/038,678 claims (Year: 2018).*
Kaylie J. Smith, et al., "Spherical, particulate poly(ether ketone ketone) by a Friedel Crafts dispersion polymerisation", The Royal Society of Chemistry, RSC Advances, Jan. 25, 2016, pp. 13809-13819, vol. 6.
European Search Report of European Patent Application No. 17 30 6045, dated Dec. 21, 2017.

* cited by examiner

PROCESS FOR PRODUCING POLYETHER KETONE KETONE

CROSS REFERENCE TO RELATED APPLICATIONS

The present application claims the benefit of European Application No. 17306045, filed on Aug. 4, 2017. The entire contents of European Application No. 17306045 are hereby incorporated herein by reference in their entirety.

TECHNICAL FIELD

The present application relates to a method for manufacturing polyether ketone ketone polymers by electrophilic substitution.

TECHNICAL BACKGROUND

Polyether ketone ketone (PEKK) polymers have a number of properties which make them useful for applications involving exposure to high temperature or to high mechanical or chemical stress. They are for instance useful in the aerospace industry, in off-shore drilling and in medical devices.

One known route for manufacturing polyether ketone ketone polymers relies on nucleophilic substitution by fluorinated monomers. This process necessitates specific fluorinated and chlorinated monomers, which must be manufactured. Further, the reaction is carried out in harsh conditions (350-400° C. in diphenylsulfone) and requires a restrictive purification steps to eliminate salts and solvent.

Another route for preparing polyether ketone ketone relies on electrophilic substitution reaction between aromatic acid chlorides and aromatic ethers in presence of a Lewis acid. This process is described in U.S. Pat. Nos. 4,841,013; 4,816,556; 4,912,181; 4,698,393; 4,716,211 and WO 2011/004164. This route allows for a reaction at moderate temperature (−20-120° C.), which limits production of by-products. Furthermore, both the monomers and solvents are readily available.

The method may more specifically rely on 1,4-bis(4-phenoxybenzoyl)benzene (EKKE) as a starting material. This compound can be prepared by reacting terephthaloyl chloride and diphenyl ether in the presence of a Lewis acid such as aluminum trichloride ($AlCl_3$). The crude solid obtained is then decomplexed using a protic solvent, washed to remove any residual reactants and side products, and subsequently dried and ground.

Subsequent reaction of 1,4-bis(4-phenoxybenzoyl)benzene with a mixture of isophtaloyl and terephtaloyl chloride in the presence of a Lewis acid leads to the formation of a polyether ketone ketone-Lewis acid complex. After polymerization, the complex is dissociated by contacting with a protic solvent, so as to recover free polyether ketone ketone, mostly in a solid precipitated form. The crude polyether ketone ketone is then separated from the product mixture by a solid/liquid separation step.

A crucial problem faced in the industrial production of polyether ketone ketone is the cost-efficiency and the environmental impact of the process.

The U.S. Pat. No. 4,816,556 discloses the synthesis of PEKK by a reaction of terephtaloyl chloride and diphenyl ether in a solvent in the presence of aluminum chloride, followed by addition of isophtaloyl chloride and further aluminum chloride in solvent. The mechanical properties of PEKK thus produced is however generally not satisfactory due to low molecular weight. Further, the color and viscosity of such PEKK may be altered when heated at or above its melting temperature, for instance during conventional transformation processes.

According to U.S. Pat. No. 3,767,620, the thermal stability of PEKK polymer can be improved by chemically partially reducing the phenylenexanthydrol endgroups. This solution is however not entirely satisfactory, since the additional reduction step is lengthy, difficult to implement on an industrial scale and because it adds a further step to the process.

Document WO 95/23821 suggests to increase molecular weight of PEKK polymers by conducting the polymerization in the presence of a dispersant that has pendant groups which comprise Lewis bases and that is thus compatible with the reaction mixture but not with the polymer. However, such dispersant must be removed subsequently since any residues may affect the thermal stability at the high temperatures required to melt PEKK polymers.

There is thus a need for a method for manufacturing polyether ketone ketone with a high molecular weight that allows for a high purity and a high yield, which can be implemented at the industrial scale in an economically realistic manner.

A particular issue in that respect within the production of polyether ketone ketone by electrophilic substitution is the large quantity of Lewis acid used.

Indeed, the process implies two successive Friedel-Crafts reactions, and the Lewis acid is thus required twice as a catalyst. Furthermore, the catalyst is required in a near-stoichiometric quantity. As a consequence, about 2 tons of aluminum trichloride can be necessary to produce 1 ton of PEKK polymer.

Such a large quantity of catalyst entails high costs. A further issue is the volume of catalyst-loaded effluents that are produced. The handling, storage and treatment of these effluents weigh on the economical balance of the process and are not desirable from an environmental point of view.

SUMMARY

Embodiments of the present invention are based on the finding that it is possible to isolate and purify the intermediate 1,4-bis(4-phenoxybenzoyl)benzene (EKKE) in form of its complex with a Lewis acid. Said purified intermediate is useful notably for the production polyether ketone ketone, without prior decomplexation.

Indeed, it has been found that it is possible to purify the EKKE-Lewis acid complex so as to eliminate any impurities which could affect the subsequent polymerization, such as the residual starting compounds, side products such as 4-(4-phenoxy benzoyl)benzoic acid and corresponding esters, and molecules containing xanthydrol moieties.

The use of the purified EKKE-Lewis acid complex further reduces the quantity of catalyst required and effluents produced, and thereby allows substantial cost savings.

Further, a solution has been found to assess the quantity of EKKE present in the EKKE-Lewis acid complex, so as to control the ratio of reactants in the polymerization step. The EKKE-Lewis acid complex can then be directly introduced in the polymerization step to yield PEKK of the required molecular weight and purity. For example, the PEKK may have an ash content of preferably less than 0.5 wt. %, preferably less than 0.3 wt. % and in particular less than 0.1 wt. %. The ash content is measured by determining the residual mass of a PEKK sample of a given weight after calcination in a furnace at 600° C. during 24H and dividing said residual mass by the mass of the PEKK sample before calcination. For example, the PEKK may have a molecular weight such as its inherent viscosity in 96% sulfuric acid according to ISO 307 is between 0.5 and 1.5 dL/g, preferably between 0.6 and 1.2 dL/g, and more preferably between 0.7 and 1.1 dL/g.

Embodiments of a method of the invention have several advantages. In particular, it eliminates the decomplexation step of 1,4-bis(4-phenoxybenzoyl)benzene (EKKE) and the subsequent drying step. This reduces the number of unit operations, thereby improving productivity. It also substantially reduces the quantity of Lewis acid and solvents required for the process, leading to an important cost reduction. Further, embodiments of a method of the invention significantly reduce the volumes of effluents charged with Lewis acid, which allows for savings in handling, storage and treatment, and importantly also reduces its environmental impact.

Embodiments of the present invention thus provide a method for the manufacture of polyether ketone ketone having a high molecular weight that allows for a high purity and a high yield, and more specifically, a method that may be implemented at the industrial scale in an economically realistic manner. For example, the overall yield may be at least 60%, preferably at least 70%, more preferably at least 80%, more preferably at least 90%, and even more preferably at least 95%.

It is thus a first object of the invention to provide a method for the manufacture of polyether ketone ketone (PEKK), comprising:
(i) providing a 1,4-bis(4-phenoxybenzoyl)benzene-Lewis acid complex;
(ii) purifying said 1,4-bis(4-phenoxybenzoyl)benzene-Lewis acid complex;
(iii) reacting said 1,4-bis(4-phenoxybenzoyl)benzene-Lewis acid complex with at least one difunctional aromatic acyl chloride in a reaction solvent and optional additional Lewis acid to obtain a product mixture comprising a PEKK-Lewis acid complex; and
(iv) decomplexing the PEKK-Lewis acid complex to obtain a PEKK polymer.

According to a preferred embodiment, step (i) of the method comprises:
(a) providing a reactant mixture comprising terephthaloyl chloride and diphenyl ether in a reaction solvent; and
(b) adding a Lewis acid to the reactant mixture, so as to obtain a product mixture comprising 1,4-bis(4-phenoxybenzoyl)benzene-Lewis acid complex.

According to a preferred embodiment, the 1,4-bis(4-phenoxybenzoyl)benzene-Lewis acid complex is purified using ortho-dichlorobenzene.

According to a preferred embodiment, the ortho-dichlorobenzene is recycled ortho-dichlorobenzene.

According to a preferred embodiment, step (iv) of the method comprises:
(a) contacting the obtained product mixture with a protic solvent so as to decomplex the PEKK-Lewis acid complex, whereby a dispersion is obtained that comprises a liquid phase comprising Lewis acid and a solid phase comprising PEKK; and
(b) separating the solid phase of the dispersion from the liquid phase, so as to recover a crude PEKK and an effluent containing Lewis acid.

According to a preferred embodiment, the effluent containing Lewis acid is recycled for use, for example, in step (ia) and/or in step (iii).

According to a preferred embodiment, the at least one difunctional aromatic acyl chloride is selected from the group consisting of terephtaloyl chloride, isophtaloyl chloride, and mixtures thereof.

According to a preferred embodiment, the reaction solvent in step (ia) and step (iii) is ortho-dichlorobenzene, respectively.

According to a preferred embodiment, the Lewis acid is aluminum trichloride.

According to a preferred embodiment, the protic solvent in step (iva) is an aqueous solution, which preferably has a pH of not more than 5, more preferably not more than 3 and most preferably not more than 2.

According to a preferred embodiment, the method of the invention further comprises after step (iv) one or more steps of washing the crude PEKK in a protic solvent, preferably methanol, and subjecting the resulting mixture to a further solid/liquid separation.

According to a preferred embodiment, the method of the invention further comprises after step (iv) one or more steps of washing the crude PEKK with a protic solvent, preferably water, and subjecting the resulting mixture to a further solid/liquid separation.

According to a preferred embodiment, step (iii) and each subsequent washing step of the method of the invention is performed in a centrifugal filtration device, without removing the PEKK between subsequent steps.

According to a preferred embodiment, the method of the invention further comprises a subsequent step of drying the PEKK.

According to a second aspect, the invention further provides a composition comprising at least 40 wt. % of 1,4-bis(4-phenoxybenzoyl)benzene-Lewis acid complex and an anhydrous aprotic solvent or solvent mixture, characterized in that it comprises less than 1 wt. %, preferably less than 0.5 wt. % and in particular less than 0.1 wt. % of molecules comprising xanthydrol groups.

According to a final aspect, the invention further provides the use of said composition for the manufacture of polyether ketone ketone (PEKK).

DETAILED DESCRIPTION OF EMBODIMENTS

Figure 1:
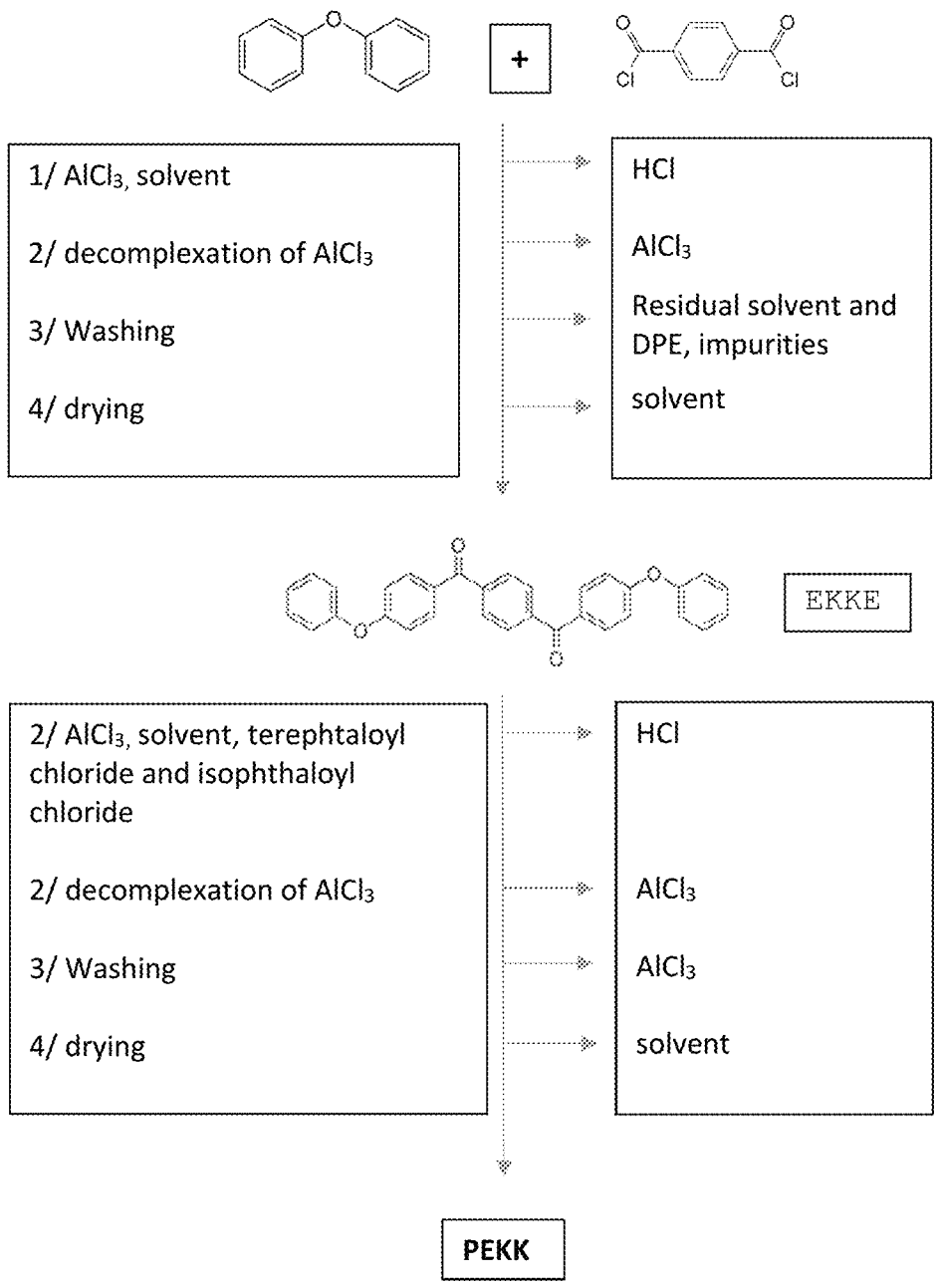
FIG. 1: is a process chart of the production of polyether ketone ketone (PEKK) where the intermediate compound 1,4-bis(4-phenoxybenzoyl)benzene (EKKE) is isolated.

Embodiments of the invention will now be described in more detail in the following description.

The polyaryl ether ketones, also known as PAEK, prepared according to the invention correspond to the following formula:

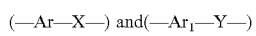

in which:
Ar and $Ar_1$ each denote a divalent aromatic radical;
Ar and $Ar_1$ may be chosen, preferably, from 1,3-phenylene, 1,4-phenylene, 4,4'-biphenylene, 1,4-naphthylene, 1,5-naphthylene and 2,6-naphthylene;

The polyether ketone ketone (PEKK) comprises units of the following formulas:

$$(-Ar-X-) \text{ and } (-Ar_1-Y-) \quad \text{Formula I}$$

wherein:
Ar and $Ar_1$ represent each a divalent aromatic radical and are preferably selected among 1,3-phenylene and 1,4-phenylene;
X represents an electron-withdrawing group which is preferably a carbonyl group; and
Y represents an oxygen atom.

Notably, the polyether ketone ketone comprises moieties of formula II A, of formula II B or a mixture thereof:

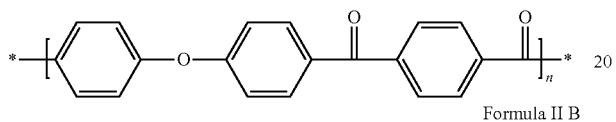

Formula II A

Formula II B

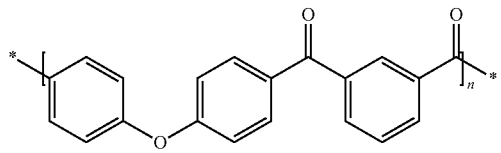

The polyether ketone ketone may consist of said moieties of formula IIA and/or IIB.

Alternatively, the polyether ketone ketone may comprise other aromatic moieties of the formula I above, notably moieties where Ar and $Ar_1$ may also be selected from bicyclic aromatic radicals such as 4,4'-diphenylene or divalent fused aromatic radicals such as 1,4-naphtylene, 1,5-naphtylene and 2,6-naphtylene.

According to a convenient route to make polyether ketone ketone, 1,4-bis(4-phenoxybenzoyl)benzene is reacted with at least one difunctional aromatic acyl chloride.

1,4-bis(4-phenoxybenzoyl)benzene, also designated EKKE, is the compound of formula III:

(III)

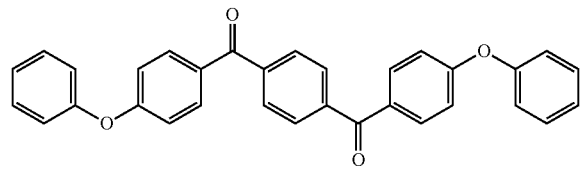

The compound of formula (III) is made by reacting terephthaloyl chloride (preferred IUPAC name: benzene-1,4-dicarbonyl dichloride) with diphenyl ether (preferred IUPAC name: 1,1'-Oxydibenzene) in a solvent and in the presence of a Lewis acid, acting as a Friedel-Crafts catalyst. The reaction results in the production of 1,4-bis(4-phenoxybenzoyl)benzene which is predominantly in the form of a complex with the Lewis acid.

It is believed that the reaction comprises two stages. In the first stage, one molecule of terephthaloyl chloride reacts with one molecule of diphenyl ether to form the intermediate 4-(4-phenoxybenzoyl)benzoyl chloride of formula IV, which is called an "active intermediate":

(IV)

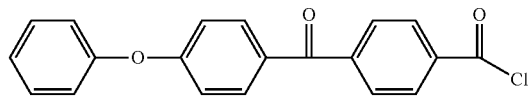

Then one molecule of the active intermediate of formula IV reacts with another molecule of diphenyl ether to form the desired product of formula III.

During the reaction, 4-(4-phenoxybenzoyl)benzoic acid of formula IVa can also be produced to some extent (notably from the active intermediate of formula IV):

(IVa)

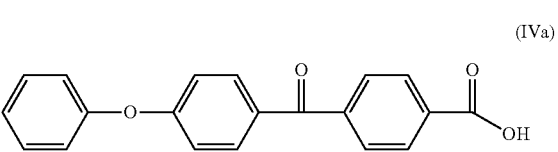 [SMILES: O=C(O)c1ccc(C(=O)c2ccc(Oc3ccccc3)cc2)cc1]

The corresponding 4-(4-phenoxybenzoyl)benzoic acid ester can be formed either directly from the acyl chloride of formula IV or from the carboxylic acid of formula IVa. The acid form and/or the ester form of the intermediate can be formed during the reaction but is primarily formed from the remaining active intermediate during subsequent workup (e.g., when the product mixture is mixed with a protic solvent for decomplexation).

In the method according to the present invention, the decomplexation step may be eliminated, and there is thus little if no conversion of the active intermediate into 4-(4-phenoxybenzoyl)benzoic acid or corresponding ester. The absence of decomplexation with a protic solvent is a notable advantage, since such compounds act as a chain stopper and thus ultimately reduce the molecular weight of the polymer.

I. Synthesis of 1,4-Bis(4-Phenoxybenzoyl)Benzene (EKKE) in Form of a Lewis Acid Complex According to an embodiment of the invention, the 1,4-bis(4-phenoxybenzoyl)benzene (EKKE) is produced in form of a Lewis acid complex and purified without prior decomplexation.

The reaction between terephtaloyl chloride and diphenyl ether to form EKKE is performed in a reactor. The reactor can be for instance a glass reactor, a glass-lined reactor or a stainless-steel reactor.

According to some variations, the materials introduced into the reactor in the method of the invention consist essentially, or consist, of the terephtaloyl chloride and diphenyl ether, the reaction solvent and the Lewis acid.

The reaction solvent is preferably a non-protic solvent.

A protic solvent is a solvent containing at least one hydrogen atom bound to an oxygen or nitrogen atom, and which is therefore able to donate protons to reagents.

A non-protic solvent is a solvent which is not a protic solvent.

The non-protic solvent used herein can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1,2,2- tetrachloroethane, tetrachloroethylene, dichloromethane, nitrobenzene and mixtures thereof.

Ortho-dichlorobenzene is the most preferred solvent.

Lewis acids which may be used include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is particularly preferred.

According to the invention, an initial reactant mixture comprising (and preferably consisting of) terephthaloyl chloride and diphenyl ether in the reaction solvent is provided. The reactant mixture can be made by mixing the three components together, in any order. By way of example, the solvent can be introduced first in the reactor, and then the two reactants can be added to the reactor.

As a second step, the Lewis acid is added to the reactant mixture. Preferably, the Lewis acid is added as a solid. Alternatively, it can also be added as a suspension or a solution, preferably in the abovementioned solvent.

In some variations, the Lewis acid is added in a particulate form, such as in the form of granules (having, e.g., a Dv80 of more than 1 mm) or in the form of a powder (having, e.g., a Dv80 of less than 1 mm, and preferably a Dv50 of less than 0.5 mm). Dv80 and Dv50 are respectively the particle sizes at the $80^{th}$ and $50^{th}$ percentiles (in volume) of the cumulative size distribution of the Lewis acid particles. These parameters may be determined by sieving.

In some particular embodiments, the weight concentrations and weight ratios of the reactants and of the catalyst are as follows:
  the concentration of terephthaloyl chloride (relative to the sum of solvent, terephthaloyl chloride, diphenyl ether and Lewis acid introduced into the reactor) is from 3 to 12%, preferably from 5 to 10%;
  the concentration of diphenyl ether (relative to the sum of solvent, terephthaloyl chloride, diphenyl ether and Lewis acid introduced into the reactor) is from 5 to 35%, preferably from 12 to 25%;
  the concentration of Lewis acid (relative to the sum of solvent, terephthaloyl chloride, diphenyl ether and Lewis acid introduced into the reactor) is from 4 to 30%, preferably from 10 to 25%;
  the weight ratio of terephthaloyl chloride to diphenyl ether introduced into the reactor is from 0.2 to 0.6, preferably from 0.3 to 0.5;
  the weight ratio of Lewis acid to terephthaloyl chloride plus diphenyl ether introduced into the reactor is from 0.2 to 0.9, preferably from 0.3 to 0.7.

The addition of the Lewis acid is preferably performed progressively, over a period of time which can advantageously range from 5 to 600 minutes, preferably from 30 to 300 minutes.

The addition can be performed continuously or with one or more interruptions. If it is performed continuously, it can be conducted at a constant rate of addition. Alternatively, the rate of addition can vary over time.

The reactant mixture is preferably agitated during at least part of the reaction step. Thus, the reactor is preferably provided with an agitation device such as a mechanical stirrer (which may, e.g., comprise one or more impellers) or a recirculation loop with a pump.

Preferably, the reactant mixture is agitated using the agitation device during the addition of the Lewis acid.

Once the addition of the Lewis acid to the reactant mixture is complete, the reaction step may optionally comprise a step of maintaining the reactant mixture, preferably under agitation, for a certain time, in order to complete the reaction to the desired degree. Preferably, the mixture is maintained from 0 to 600 min, more preferably from 5 to 180 min.

Once the reaction has been completed to the desired degree, the reactant mixture becomes designated as a product mixture.

The reaction at stake is exothermic. Preferably, a temperature control system is provided, in order to control the temperature of the reactant mixture in the reactor, in particular during and after addition of the Lewis acid. The temperature control system may in particular comprise a temperature sensor within the reactor and may be configured to cool and/or to heat the reactant mixture. Preferably, it is at least configured to cool the reactant mixture.

Devices for heating and/or cooling the reactant mixture may include a heat exchanger inside the reactor or in a recirculation loop, or a heat exchange fluid circuit in the jacket of the reactor.

When the temperature of the reactant mixture increases during the step of adding the Lewis acid, this can be achieved in three different manners:
  by heating the reactant mixture (while preferably also controlling the rate of addition of the Lewis acid, so as to achieve a targeted increase in temperature);
  by simply controlling the rate of addition of the Lewis acid so as to achieve a targeted increase in temperature, without providing external cooling or heating; or
  by cooling the reactant mixture, while also controlling the rate of addition of the Lewis acid, so as to achieve a targeted increase in temperature According to a preferred embodiment, the reactant mixture is cooled during and possibly also after the step of adding the Lewis acid, in order to prevent an excessively large or rapid increase in temperature of the reactant mixture as the reactants start reacting with each other.

Preferably, the temperature of the reactant mixture is greater than 5° C. during at least part of the step of adding the Lewis acid to the reactant mixture. In particular variations of the invention, the temperature of the reactant mixture is at least 10° C., or at least 15° C., or at least 20° C., or at least 25° C., or at least 30° C., or at least 35° C., or at least 40° C., or at least 45° C., or at least 50° C., or at least 55° C., or at least 60° C., during at least part of the step of adding the Lewis acid to the reactant mixture.

Conducting the reaction step at a relatively high temperature results in an increase in the yield of 1,4-bis(4-phenoxybenzoyl)benzene, without any significant increase in the level of by-product impurities such as 4-(4-phenoxy benzoyl)benzoic acid and corresponding esters and molecules containing xanthydrol moieties.

On the other hand, the temperature during the step of adding the Lewis acid to the reactant mixture should preferably remain below a certain threshold in order to avoid any significant polymerization of the reactants into a PEKK polymer.

Furthermore, the temperature during the step of adding the Lewis acid to the reactant mixture should remain below the boiling temperature of the solvent.

It is possible to operate the reactor in a pressurized manner so that the temperature in the reactor can reach a higher value without causing the solvent to boil. In this case, the pressure in the reactor can range from 1 bar (atmospheric pressure) to 6 bar, preferably from 1.5 bar to 3 bar.

Alternatively, and preferably, the reaction is performed at atmospheric pressure.

According to some variants of the invention, the temperature of the reactant mixture does not exceed 100° C., preferably 90° C., more preferably 80° C., even more preferably 70° C., during the step of adding the Lewis acid.

The temperature of the reactant mixture can remain constant during the step of adding the Lewis acid, for example, within +/−5° C., or +/−2° C., or +/−1° C. Alternatively, it can vary during this step.

In preferred variations, the temperature of the reactant mixture increases during the step of adding the Lewis acid, i.e. the final temperature is greater than the initial temperature.

In some embodiments, the temperature difference ΔT between the final temperature and the initial temperature is from 1 to 70° C., preferably from 5 to 60° C., more preferably from 10 to 50° C., and in particular from 20 to 40° C.

In some variations, the temperature of the reactant mixture continuously increases from the initial temperature to the final temperature. Alternatively, the temperature of the reactant mixture may comprise one or more increase stages and one more plateau stages during the step of adding the Lewis acid. In particular, the temperature of the reactant mixture may initially increase during a first part of the step of adding the Lewis acid, from the initial temperature to the final temperature, and then plateau at the final temperature during a second part of the step of adding the Lewis acid. In this case, the plateaued temperature may be set with a precision of, e.g., +/−5° C., or +/−2° C., or +/−1° C.

There is no limitation as to the temperature of the reactant mixture during the optional step of maintaining the reactant mixture, after the addition of the Lewis acid. In some variations of the invention, the temperature of the mixture is maintained at the final temperature described above. In other variations, it increases or decreases relative to the final temperature.

II. Purification of the Lewis Acid Complex of EKKE

After the reaction has been completed to the desired degree, the EKKE-Lewis acid complex obtained may be separated from the product mixture, and in particular from the solvent, excess catalyst and unreacted reactants as well as by-products, and be subsequently purified.

Upon contact with water or other protic solvents such as alcohols, the EKKE-Lewis acid is decomplexed and forms 1,4-bis(4-phenoxybenzoyl)benzene. Oxygen can also affect its purity. It is therefore preferred to carry out the separation and purification steps described below under suitable protection, such as under a blanket of dry nitrogen or argon. Further, it is preferred to dry all reactants and solvents prior to use.

In order to recover the crude EKKE-Lewis acid complex from the reaction mixture, it is advantageous to perform a solid/liquid separation step, which is preferably a filtration step, a centrifugation step or a sedimentation step, and more preferably a filtration step.

The filtration step can be performed for example on a filter press, a Nutsche filter, a belt filter, a candle filter, a basket centrifuge, a decanter centrifuge, either in batch or continuous mode. In a preferred embodiment, filtration is performed on a centrifugal filtration device. The centrifugal filtration device may in particular have a horizontal axis or a vertical axis.

Centrifugal filtration is preferably performed at an acceleration rate of from 2 to 1500 g, more preferably of from 5 to 1000 g, and most preferably of from 10 to 800 g. Different acceleration values or ranges may be used during successive phases of centrifugal filtration, such as a loading phase, a washing phase and/or a dewatering phase. By way of example, a low acceleration may be applied first, followed by higher acceleration. Throughout the present application, unless indicated otherwise, the acceleration rate considered for a variable acceleration rate embodiment is the maximum acceleration rate.

The dry solid matter content of the filtered product at the end of the filtration is preferably from 30 wt. % to 99 wt. %, more preferably from 40 wt. % to 95 wt. %, even more preferably from 50 to 90 wt. %, and most preferably from 60 to 80 wt. %.

The separation temperature can, e.g., generally range from −20 to 0° C., or from 0 to 20° C., or it can be at least 20° C.

A crude solid Lewis acid complex of 1,4-bis(4-phenoxybenzoyl)benzene, together with residual impurities, is recovered after the solid/liquid separation step.

In order to achieve a high purity of the final PEKK, it is desirable to eliminate impurities, in particular the residual diphenyl ether, molecules containing xanthydrol moieties, 4-(4-phenoxybenzoyl)benzoic acid and 4-(4-phenoxybenzoyl)benzoic acid esters.

According to the invention, said solid is purified before polymerization. Preferably, the solid is purified by washing it in a suitable purifying solvent.

A suitable purifying solvent is preferably a non-protic solvent. Such non-protic solvent as used herein can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1,2,2-tetrachloroethane, tetrachloroethylene, dichloromethane, nitrobenzene, heptane, cyclohexane, hexane, pentane, diethylether and mixtures thereof.

Ortho-dichlorobenzene is the most preferred purifying solvent. Indeed, the Lewis acid complexes of 1,4-bis(4-phenoxybenzoyl)benzene and of the active intermediate have a low solubility in this solvent, while other organic impurities such as diphenylether and molecules containing xanthydrol moieties have a much higher solubility in this solvent.

The weight ratio of crude solid Lewis acid complex of 1,4-bis(4-phenoxybenzoyl)benzene to purifying solvent used at this washing step may be, e.g., from 0.3 to 20, preferably from 0.6 to 10, more preferably from 1 to 5.

The washing step may be performed by mixing the crude solid Lewis acid complex of 1,4-bis(4-phenoxybenzoyl)benzene with the purifying solvent in a vessel. The duration of such a washing step may be, e.g., from 5 to 900 min, preferably from 15 to 300 min, more preferably from 45 to 120 min.

If use is made of a centrifugal filtration device, washing and filtering may be performed concomitantly in this device.

The washing step and the subsequent or concomitant solid/liquid separation step are preferably performed at a temperature that ranges from −20 to 0° C., or from 0 to 20° C., or from 20° C. to 40° C., or it can be at least 40° C.

Temperature control during these steps can be performed as described above.

After the washing step or concomitantly with the washing step, another solid/liquid separation step may be performed.

The washing and solid/liquid separation steps may optionally be repeated one or more times, in exactly the same manner or in a different manner. For example, different purifying solvents, different washing durations and/or different temperatures may be used in the various washing and solid/liquid separation steps.

If centrifugal filtration is used, at each centrifugal filtration, an acceleration rate of preferably from 2 to 1500 g, more preferably of from 5 to 1000 g, and most preferably of from 10 to 800 g, may be used.

If centrifugal filtration is used, at each centrifugal filtration, the dry solid matter content of the filtered product at the end of the filtration is preferably from 30 wt. % to 99 wt. %, more preferably from 40 wt. % to 95 wt. %, even more preferably from 50 to 90 wt. %, and most preferably from 60 to 80 wt. %.

After the last solid/liquid separation, the recovered solid may be dried, preferably at atmospheric pressure or under vacuum in an oven or a dryer.

Ultimately, the Lewis acid complex of 1,4-bis(4-phenoxybenzoyl)benzene is recovered in a substantially pure form, i.e. at a purity of preferably at least 90%, more preferably at least 95%, more preferably at least 97%, more preferably at least 98.5 wt. %, more preferably at least 99.0 wt. % and more preferably at least 99.5 wt. %.

In order to control the ratio of reactants in the subsequent polymerization reaction, one may assess the purity of the complex obtained. The purity and therefore the amount of the complex may be determined by a number of methods, including nuclear magnetic resonance, spectrometry (NIR, MIT, RAMAN, UV . . . ), differential scanning calorimetry, gas chromatography or high-performance liquid chromatography (HPLC). Within the present application, said purity is determined by HPLC.

The purified Lewis acid complex of 1,4-bis(4-phenoxybenzoyl)benzene obtained according to the process of the invention can be used to produce a polyaryl ether ketone, in particular a polyether ketone ketone (PEKK) polymer.

III. Synthesis of PEKK

In order to make the PEKK polymer, the Lewis acid complex of 1,4-bis(4-phenoxybenzoyl)benzene is reacted with at least one difunctional aromatic acyl chloride.

The difunctional aromatic acyl chloride may in particular include terephthaloyl chloride, isophthaloyl chloride and more preferably a mixture of terephthaloyl chloride and isophthaloyl chloride.

The reaction is preferably implemented in a solvent. The solvent is preferably a non-protic solvent, which can in particular be selected from methylene chloride, carbon disulfide, ortho-dichlorobenzene, meta-dichlorobenzene, para-dichlorobenzene, 1,2,4-trichlorobenzene, 1,2,3-trichlorobenzene, ortho-difluorobenzene, 1,2-dichloroethane, 1,1,2,2-tetrachloroethane, tetrachloroethylene, dichloromethane, nitrobenzene and mixtures thereof. Ortho-dichlorobenzene is the most preferred solvent.

The reaction is implemented using a Lewis acid as a catalyst. In the method of the present invention, it is not necessary to add further Lewis acid since the EKKE is used in form of a Lewis acid complex. However, additional Lewis acid may be added, so as to improve yield and/or reaction speed and consequently obtain PEKK with a higher molecular weight.

The reaction is further preferably conducted in the presence of a suitable chain stopper. A chain stopper is a monofunctional compound added so as to control the chain length of the polyether ketone ketone. Suitable chain stoppers in the present reaction are notably benzoyl chloride or phenoxybenzophenone.

The reaction between the at least one difunctional aromatic acyl chloride and 1,4-bis(4-phenoxybenzoyl)benzene to obtain PEKK is performed in a reactor. The reactor can be for instance a glass reactor, a glass-lined reactor or a stainless steel reactor. The polymerization can be implemented in the same reactor as the one used for the production of 1,4-bis(4-phenoxybenzoyl)benzene. But more preferably it is implemented in one or more distinct reactors.

According to some variations, the materials introduced into the reactor in the method of the invention consist essentially, or consist, of the Lewis acid complex of 1,4-bis(4-phenoxybenzoyl)benzene and the at least one difunctional aromatic acyl chloride, the reaction solvent, optional additional Lewis acid and the chain stopper.

According to the invention, an initial reactant mixture comprising (and preferably consisting of) terephthaloyl chloride, isophtaloyl chloride and the Lewis acid complex of 1,4-bis(4-phenoxybenzoyl)benzene in the reaction solvent is provided. The reactant mixture can be made by mixing the three components together, in any order. By way of example, the solvent can be introduced first in the reactor, and then the two reactants can be added to the reactor.

The polymerization can be carried out at a temperature ranging from, e.g., 50 to 120° C.

The conditions and equipment are preferably chosen in such a way that the crude polymer is obtained in granular form (having, e.g., a Dv80 of more than 1 mm). If desired, the crude polymer may be granulated using suitable milling equipment.

The method of the invention further preferably comprises steps for purifying the crude polyether ketone ketone present in the product mixture, and in particular from the solvent, catalyst and unreacted reactants as well as by-products.

In particular, said purification comprises the step of contacting the product mixture with a protic solvent, so as to recover a first phase containing the Lewis acid and a second phase containing the crude polyether ketone ketone. The relative weight ratio of protic solvent and crude PEKK is preferably from 5 to 100, more preferably from 15 to 50.

The protic solvent can in particular be an organic solvent, such as methanol, ethanol, isopropanol or acetic acid. Methanol is preferred as an organic solvent.

Alternatively, the protic solvent can be an aqueous solution. The aqueous solution can be simply water. Alternatively, it can be an acidic solution, such as a solution of hydrochloric acid. A preferred aqueous solution is water acidified by addition of up to 10 wt. %, preferably up to 0.4 wt. % of suitable acid, for instance concentrated hydrochloric acid. Preferably, the pH of the aqueous solution is not more than 7, preferably not more than 6, or not more than 5, or not more than 4, or not more than 3, or not more than 2. The dissociation of the polyether ketone ketone-Lewis acid complex is more efficient when an acidic solution is used.

Mixtures of the above solvents can also be used, such as an aqueous-organic solvent, e.g., an aqueous solution mixed with methanol. The proportions of the alcohol in the mixture should be sufficient to allow for good elimination of the aluminum but however limited so as to avoid side reactions. A good compromise is a mixture of aqueous solution and alcohol comprising 95 to 60 wt. %, preferably 80 to 95 wt. %, of alcohol.

A first possibility for contacting the polyether ketone ketone-Lewis acid complex with the protic solvent is to add the protic solvent to the product mixture, for example directly in the reactor. The addition is preferably performed progressively, over a period of time which can advantageously range from 30 to 180 minutes, preferably from 30 to 90 minutes at a temperature >50° C., preferably between 60 and 160° C.

A second possibility is to provide the protic solvent in a separate vessel and to subsequently add the product mixture to the protic solvent. The addition is preferably performed progressively, over a period of time which can advantageously range from 30 to 180 minutes, preferably from 30 to 90 minutes at a temperature >50° C., preferably between 60 and 160° C.

A third possibility is to simultaneously feed the protic solvent and the product mixture into a reactor or a pipe.

For all possibilities, the mixture of protic solvent and product mixture is preferably agitated, using, e.g., an agitation device such a mechanical stirrer (which may comprise one or more impellers) or a recirculation loop with a pump.

Once the total of the product mixture and of the protic solvent have been contacted, the mixture of both can be maintained, preferably with agitation, for a period of time of, e.g., from 10 to 240 minutes, preferably from 30 to 120 minutes at a temperature >75° C., preferably between 80 and 160° C.

Temperature may optionally be controlled at this stage, and for instance the mixture may be cooled.

In an alternative variation, the temperature is not controlled at this stage, and it thus rises, possibly up to the boiling point of one or more of the solvents (including, e.g., water) present in the mixture, and even above 100° C. if the reaction is carried out under pressure. The steam thus generated can be collected and then treated and/or recycled or disposed of. The mixture can optionally cool down (or be actively cooled down) after this exothermic surge. Temperature control and cooling devices as already mentioned above may be used to this end.

It has been found that the morphology of the solid form of the crude polyether ketone ketone thus recovered is an important parameter for the efficiency of the solid/liquid separation step. Indeed, after dissociation of the complex, the crude polyether ketone ketones tend to form a gel containing high amounts of liquid.

So as to facilitate separation from the surrounding liquid, the polymer may be granulated if it is not obtained in this form.

The crude polymer granules obtained are porous and contain high amounts of liquid, and therefore are difficult to separate by conventional filtration.

The solid/liquid separation step to recover polyether ketone ketone from the mixture is preferably performed by filtration in a centrifugal filtration device.

The solid/liquid separation step is performed at a temperature that ranges from 5° C. to 90° C. A separation temperature of at least 20° C. is preferred, in particular if an aqueous solution is used as a protic solvent.

The acceleration rate of the centrifuge during the solid/liquid separation step can be constant or variable. According to a preferred embodiment, the acceleration rate is variable. In particular, the acceleration rate may be increased at the end of the solid/liquid separation step.

The acceleration rate for the solid/liquid separation is preferably at least 300 g, even more preferred at least 500 g, in particular at least 800 g and particularly preferred at least 1000 g.

At the end of the centrifugal filtration, the acceleration rate may be advantageously increased. As an example, the acceleration rate can be raised during the last quarter, preferably the last 20%, the last 15% or the last 10% of the entire duration of the centrifugal filtration. The increased acceleration rate is preferably at least 500 g and more preferably at least 800 and in particular at least 1200 g.

The duration of the centrifugal filtration is generally between 15 to 60 minutes, preferably 30 minutes or less and in particular 15 minutes or less.

If advantageous, it is possible to build the cake by charging the device in several steps. However, it is generally preferred that the filtration be carried out in one batch.

The dry solid matter content of the crude polyether ketone ketone product at the end of the solid/liquid separation step by centrifugal filtration is preferably from 10 wt. % to 90 wt. %, preferably from 20 to 80 wt. % and in particular from 30 to 60 wt. %.

Solid polyether ketone ketone, together with residual impurities, is recovered after the solid/liquid separation step.

The liquid effluents, containing the first phase and the second phase are separated so as to be recovered separately, preferably by decantation. A surfactant can be added in order to facilitate the phase separation.

The liquid effluents containing the Lewis acid may be submitted to suitable treatments so as to allow their reuse or recycling into the process. In particular, the effluents comprising Lewis acid may be recycled, notably as a flocculation agent for water treatment.

In preferred variations of the process, said crude polyether ketone ketone is further purified by washing with one or more protic solvents.

The protic solvent at this stage is preferably water or an aqueous solution. However, in alternative variations, the protic solvent at this stage may be an organic solvent, optionally mixed with water. Aliphatic straight or branched alcohols such as methanol, ethanol and isopropanol are particularly preferred organic solvents. These organic solvents may optionally be mixed with another and/or with water.

The weight ratio of protic solvent used at this stage to crude polyether ketone ketone may be, e.g., from 2 to 30, preferably from 3 to 10.

After the washing step or concomitantly with the washing step, another solid/liquid separation step may be performed.

The washing step may be performed by mixing the crude polyether ketone ketone recovered at the previous step with the protic solvent in a vessel. The duration of such a washing step may be, e.g., from 15 min to 240 min, preferably from 15 to 120 min.

However, in preferred variations, use is made of a centrifugal filtration device, so that washing and solid/liquid separation may be performed concomitantly in this device, without re-suspending the product.

The acceleration rate of the centrifuge during the washing and subsequent solid/liquid separation step can be constant or variable. According to a preferred embodiment, the acceleration rate is lower during the washing step, so as to increase the contact time. However, the acceleration rate may be increased when starting the subsequent solid/liquid separation step and/or at the end thereof.

The acceleration rate of the centrifuge for the washing is preferably 500 g or less, even more preferred 300 g or less, in particular 100 g or less. The acceleration rate for the subsequent solid/liquid separation is preferably at least 500 g, even more preferred at least 800 g, in particular at least 1000 g.

The washing step and the subsequent or concomitant solid/liquid separation step are preferably performed at a temperature of at least 20° C.

It may be advantageous to operate at a higher temperature during the washing step and associated subsequent or concomitant solid/liquid separation step than during the initial solid/liquid separation step. It is thus possible to operate at a temperature up to the boiling point of the protic solvent which is used.

Possible temperature ranges for these steps are in particular from 20 to 25° C., from 25 to 30° C., from 30 to 35° C., from 35 to 40° C., from 40 to 45° C., from 45 to 50° C., from 50 to 55° C., and from 55 to 60° C. and even up to 100° C. for water.

The washing step and the associated solid/liquid separation (preferably including centrifugal centrifugation) step may optionally be repeated one or more times, in exactly the same manner or in a different manner. For example, different protic solvents, different washing durations and/or different temperatures may be used in the various washing and solid/liquid separation steps.

After the last solid/liquid separation (preferably including centrifugal filtration), the recovered solid may be dried.

The drying step can be realized in a conventional manner, for instance at a temperature ranging from 100° C. to 280° C., and under atmospheric pressure or, preferably, under reduced pressure, for instance at a pressure of 30 mbar.

Ultimately, the polyether ketone ketone obtained is substantially pure. In particular, the ash content of the polyether ketone ketone is preferably less than 0.5 wt. %, preferably less than 0.3 wt. % and in particular less than 0.1 wt. %. The ash content is measured by determining the residual mass of a PEKK sample of a given weight after calcination in a furnace at 600° C. during 24H and dividing said residual mass by the mass of the PEKK sample before calcination.

The polyether ketone ketone obtained according to the invention can subsequently be compounded and/or formed into the appropriate shape in view of further transformation and final use.

EXAMPLES

Comparative Example 1: PEKK from EKKE

At first, EKKE is produced using the following procedure:

In a 2 L reactor equipped with a mechanical stirrer, with a nitrogen inlet and outlet going to a scrubber system, we introduce 1066 g of ortho-dichlorobenzene, 92.7 g of terephthaloyl chloride and 233 g of diphenylether. After full solubilization, the mixture is set at 35° C. While keeping this temperature at 35° C., 198 g of aluminum trichloride is slowly added over 3 h to the reaction mixture. After completion of aluminum trichloride addition, the mixture is kept agitated at 35° C. during 3 h to finish the reaction.

The mixture is then poured in a second reactor containing 830 g of water containing 3% HCl. After completion of this step, the mixture is settled during 3 h h so that the aqueous phase can decant and be removed by suction. A second 3% HCl aqueous phase in then added, stirred then settled during 1 h for decantation. This second acidic aqueous phase is also removed by suction. The so-obtained suspension of EKKE in organic solvent is then heated up to 120° C., and cooled down to 35° C. in 3 h. The solid obtained is then separated from the solvent in a centrifuge at 400 rpm. After removal of mother liquor, the wet powder is kept in the centrifuge and spray-washed with 1900 g of methanol at 35° C. while the centrifuge still being in rotation. The wet solid obtained is then removed from the centrifuge, having a solid content of 96% as measured by its weight loss on drying. It is then dried overnight under vacuum. 183 g of EKKE is obtained with a purity of about 99.75% as determined by HPLC.

In a 2 L reactor equipped with a mechanical stirrer, with a nitrogen inlet and outlet going to a scrubber system, we introduce 1600 g of 1,2-dichlorobenzene, 65 g of so-obtained EKKE, 10.9 g of terephthaloyl chloride, 16.6 g of isophthaloyl chloride, and 0.6 g of benzoyl chloride. The mixture is cooled down to −5 C and then 117 g of aluminum chloride is added while maintaining the temperature below 5° C. After 10 minutes, temperature of the system is increased up to 90 C at 5 C/min. The mixture is held 30 min at 90 C, and then cooled down to 30° C. At this point, 400 g of acidic water (HCl 3%) is slowly added to the mixture so that the temperature remains below 60° C.

The PEKK is recovered from the suspension by filtration under vacuum. It is then washed in the filter with 300 g of methanol. The wet PEKK obtained is removed from the filter and reslurried in 700 g of methanol in a beaker with magnetic stirring during 2 hours. After that, it is filtered a second time and rinsed a second time with 300 g of methanol. So-obtained wet PEKK is removed from the filter and reslurried in 750 g of acidic water (3% HCl) in a beaker with magnetic stirring during 2 hours. This suspension is filtered, and the solid obtained is rinsed in the filter with 450 g water, before being reslurried in 400 g of sodium hydroxide solution 0.5N during 2 hours. After filtration, the solid is rinsed with water until the pH of the filtrate becomes neutral. It is then dried overnight in a vacuum oven at 180° C.

The PEKK obtained has high molecular weight. Its inherent viscosity in sulfuric acid measured according to the standard ISO 307 is 1.00 dL/g.

Comparative Example 2: PEKK from EKKE Using Less AlCl$_3$

In a 2 L reactor equipped with a mechanical stirrer, with a nitrogen inlet and outlet going to a scrubber system, we introduce 1600 g of 1,2-dichlorobenzene, 65 g of EKKE prepared as described in the preceding example, 10.9 g of terephthaloyl chloride, 16.6 g of isophthaloyl chloride and 0.4 g of benzoyl chloride. The mixture is cooled down to −5° C. and then 81 g of aluminum chloride is added while maintaining the temperature below 5° C. After 10 minutes, temperature of the system is increased up to 90 C at 5° C./min. The mixture is held 30 min at 90° C., and then cooled down to 30° C. At this point, 400 g of acidic water (HCl 3%) is slowly added to the mixture so that the temperature remains below 60° C.

The PEKK is recovered from the suspension by filtration under vacuum. It is then washed in the filter with 300 g of methanol. The wet PEKK obtained is removed from the filter and reslurried in 700 g of methanol in a beaker with magnetic stirring during 2 hours. After that, it is filtered a second time and rinsed a second time with 300 g of methanol. The wet PEKK obtained is removed from the filter and reslurried in 750 g of acidic water (3% HCl) in a beaker with magnetic stirring during 2 hours. This suspension is filtered, and the solid obtained is rinsed in the filter with 450 g water, before being reslurried in 400 g of sodium hydroxide solution 0.5N during 2 hours. After filtration, the solid is rinsed with water until the pH of the filtrate becomes neutral. It is then dried overnight in a vacuum oven at 180° C.

The PEKK thus obtained has a low molecular weight. Its inherent viscosity in sulfuric acid measured according to the standard ISO 307 is 0.48 dL/g.

Despite a smaller amount of chain limitation agent (benzoyl chloride), the inherent viscosity of PEKK produced according to example 2 is much lower than the viscosity of the PEKK produced according to example 1. This illustrates how difficult it is to reduce the amount of aluminum chloride used for the overall synthesis of PEKK via EKKE, without decreasing also the quality of the PEKK obtained.

Comparative Example 3: PEKK from Unpurified EKKE-AlCl$_3$ Complex

In a 2 L reactor equipped with a mechanical stirrer, with a nitrogen inlet and outlet going to a scrubber system, we introduce 830 g of 1,2-dichlorobenzene (o-DCB), 47 g of diphenylether and 18.5 g of terephthaloyl chloride. After dissolution, the mixture is cooled down to 0° C. and then 48 g of AlCl3 is slowly added while keeping the temperature below 5° C. After that, the system is maintained with stirring 30 min at 0° C., obtaining an orange suspension of EKKE-AlCl$_3$ complex in the solvent mixture.
In the same reactor, 20.4 g of terephthaloyl chloride, 16.7 g of isophthaloyl chloride and 930 g of oDCB is added. Then 67 g of AlCl$_3$ is added portionwise while keeping the mixture below 5° C. After 10 minutes, temperature of the system is increased up to 90° C. at 5° C./min. The mixture is held 30 min at 90° C., and then cooled down to 30° C. At this point, 400 g of acidic water (HCl 3%) is slowly added to the mixture so that the temperature remains below 60 C. The suspension of wet PEKK obtained is purified and dried as described in example 1.

The PEKK thus obtained also has a low molecular weight, as shown by its inherent viscosity of 0.48 dL/g. This is mainly due to the xanthydrol end groups formed, as explained in patent EP 0 229 470.

Example 1: PEKK from Purified EKKE-AlCl$_3$ Complex

In a 2 L reactor equipped with a mechanical stirrer, with a nitrogen inlet and outlet going to a scrubber system, we introduce 340 g of 1,2-dichlorobenzene, 74 g of diphenylether and 29.5 g of terephthaloyl chloride. After dissolution, the mixture is cooled down to 0° C. and then 63 g of AlCl$_3$ is slowly added while keeping the temperature below 5° C. After that, the system is maintained with stirring 30 min at 0° C. and cooled down to −20° C. obtaining an orange suspension of EKKE-AlCl$_3$ complex in the solvent mixture. The agitation is stopped, the solid allowed to settle and then the liquid is removed opening slowly the bottom valve. 300 g of cold oDCB is added to the reactor and the EKKE-AlCl$_3$ complex is reslurried 10 min. It is then settled, and the liquid is removed. A second wash is performed exactly similarly.

The purified EKKE-AlCl$_3$ complex thus obtained is then reslurried in the reactor in 1600 g of oDCB at 0° C. and 11.2 g of terephtaloyl chloride and 16.8 g of isophthaloyl chloride is added. 76 g of AlCl$_3$ is added portionwise while keeping the mixture below 5° C. After 10 minutes, the temperature of the system is increased up to 90° C. at 5° C./min. The mixture is held 30 min at 90° C., and then cooled down to 30° C. At this point, 400 g of acidic water (HCl 3%) is slowly added to the mixture so that the temperature remains below 60° C. The suspension of wet PEKK obtained is purified and dried as described in example 1.

Final dry PEKK obtained has a molecular weight higher than comparative example 3, having inherent viscosity of 0.77 dL/g. The purification steps detailed here are effective in removing most of the molecules comprising xanthydrol end-group generated during the first part of the synthesis, thus enabling the formation of higher molecular weight PEKK with better properties. The PEKK also has a higher viscosity and thus molecular weight compared to a synthesis using EKKE and less AlCl$_3$ (comparative example 2).

Figure 2:
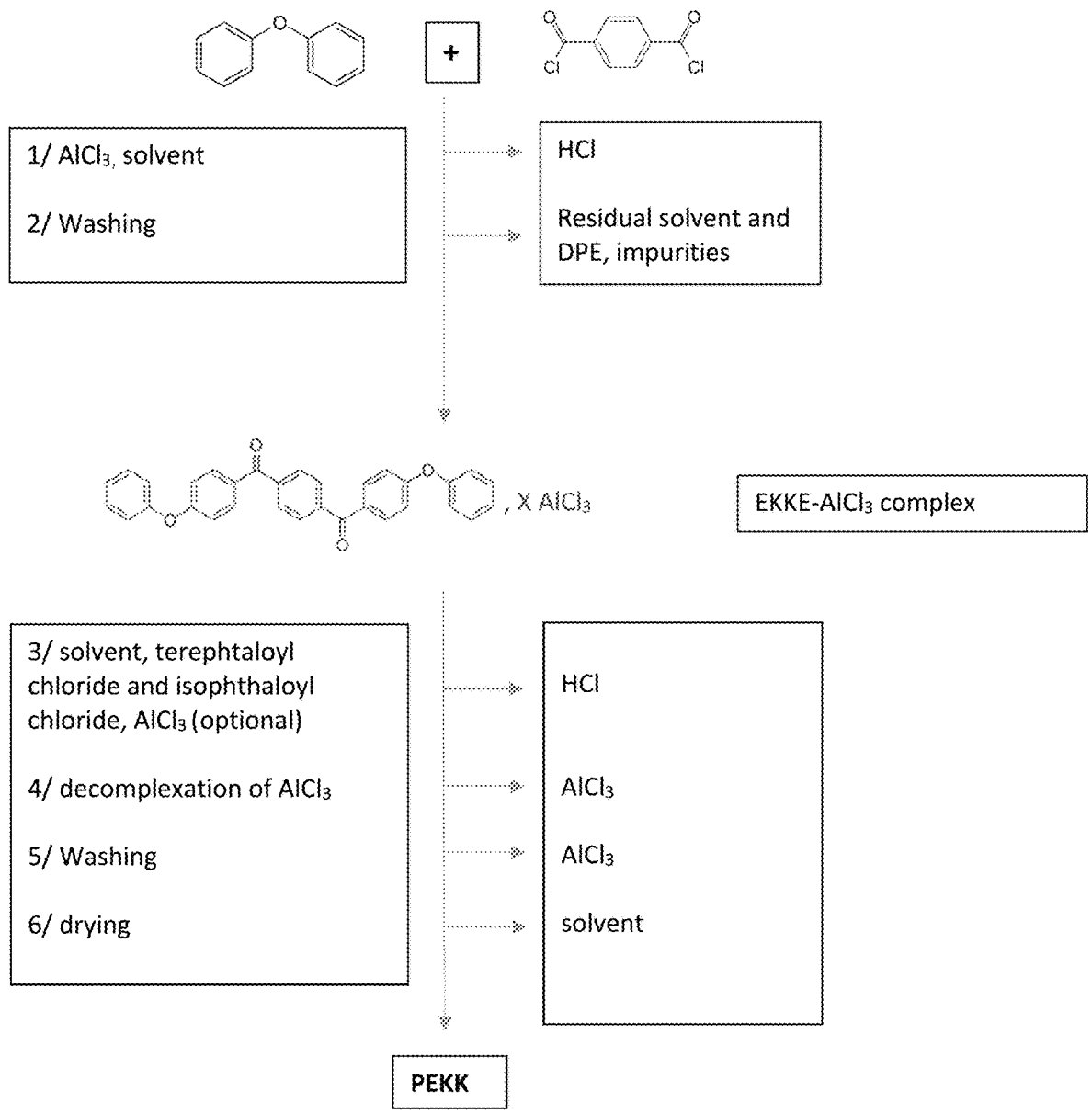
FIG. 2: is a process chart of the production of polyether ketone ketone (PEKK) according to an embodiment of the present invention, without isolation of the intermediate compound 1,4-bis(4-phenoxybenzoyl)benzene (EKKE).

As explained above, and shown in FIG. 1 and FIG. 2, the method of the invention eliminates the decomplexation step of 1,4-bis(4-phenoxybenzoyl)benzene (EKKE) and the drying step, thus reducing the number of unit operations and improving productivity. It also substantially reduces the quantity of Lewis acid and solvents required for the process, leading to an important cost reduction. Further, the method of the invention significantly reduces the volumes of effluents charged with Lewis acid, which allows for savings in handling, storage and treatment, and importantly also reduces its environmental impact. The present invention thus provides a method for the manufacture of polyether ketone ketone having a high molecular weight that allows for a high purity and a high yield, and more specifically, a method that may be implemented at the industrial scale in an economically realistic manner.

EMBODIMENTS

1. A method for the manufacture of polyether ketone ketone (PEKK), comprising:
   (i) providing a 1,4-bis(4-phenoxybenzoyl)benzene-Lewis acid complex;
   (ii) purifying said 1,4-bis(4-phenoxybenzoyl)benzene-Lewis acid complex;
   (iii) reacting said 1,4-bis(4-phenoxybenzoyl)benzene-Lewis acid complex with at least one difunctional aromatic acyl chloride in a reaction solvent and optional additional Lewis acid to obtain a product mixture comprising a PEKK-Lewis acid complex; and
   (iv) decomplexing the PEKK-Lewis acid complex to obtain a PEKK polymer.
2. The method of embodiment 1, wherein step (i) comprises:
   (a) providing a reactant mixture comprising terephthaloyl chloride and diphenyl ether in a reaction solvent;
   (b) adding a Lewis acid to the reactant mixture, so as to obtain a product mixture comprising 1,4-bis(4-phenoxybenzoyl)benzene-Lewis acid complex.
3. The method of any embodiments 1 to 2, wherein the 1,4-bis(4-phenoxybenzoyl)benzene-Lewis acid complex is purified using ortho-dichlorobenzene.
4. The method of any embodiments 1 to 3, wherein the ortho-dichlorobenzene is recycled ortho-dichlorobenzene.
5. The method of any embodiments 1 to 4, wherein step (iv) comprises:
   (a) contacting the obtained product mixture with a protic solvent so as to decomplex the PEKK-Lewis acid complex, whereby a dispersion is obtained that comprises a liquid phase comprising Lewis acid and a solid phase comprising PEKK; and
   (b) separating the solid phase of the dispersion from the liquid phase, so as to recover a crude PEKK and an effluent containing Lewis acid.
6. The method of embodiment 5, wherein the effluent containing Lewis acid is recycled.
7. The method of any embodiments 1 to 6, wherein the at least one difunctional aromatic acyl chloride is selected from the group consisting of terephtaloyl chloride, isophtaloyl chloride, and mixtures thereof.

8. The method of any one of embodiments 2 to 7, wherein the reaction solvent in step (ia) and step (iii) is ortho-dichlorobenzene, respectively.
9. The method of any one of embodiments 1 to 8, wherein the Lewis acid is aluminum trichloride.
10. The method of any of embodiments 5 to 9, wherein the protic solvent in step (iva) is an aqueous solution, which preferably has a pH of not more than 5, more preferably not more than 3 and most preferably not more than 2.
11. The method of any of embodiments 1 to 10, further comprising after step (iv) one or more steps of washing the crude PEKK in a protic solvent, preferably methanol, and subjecting the resulting mixture to a further solid/liquid separation.
12. The method of any of embodiments 1 to 11, further comprising after step (iv) one or more steps of washing the crude PEKK with a protic solvent, preferably water, and subjecting the resulting mixture to a further solid/liquid separation.
13. The method of any of embodiments 1 to 12, wherein step (iv) and each subsequent washing step is performed in a centrifugal filtration device, without removing the PEKK between subsequent steps.
14. The method of any one of embodiments 1 to 13, further comprising a subsequent step of drying the PEKK.
15. A composition comprising at least 40 wt. % of 1,4-bis(4-phenoxybenzoyl)benzene-Lewis acid complex and an anhydrous aprotic solvent or solvent mixture, characterized in that it comprises less than 1 wt. %, preferably less than 0.5 wt. % and in particular less than 0.1 wt. % of molecules comprising xanthydrol groups.
16. Use of the composition according to embodiment 15 for the manufacture of polyether ketone ketone (PEKK).

The invention claimed is:
1. A method for the manufacture of polyether ketone ketone (PEKK), comprising:
   (i) providing a 1,4-bis(4-phenoxybenzoyl)benzene-Lewis acid complex;
   (ii) purifying said 1,4-bis(4-phenoxybenzoyl)benzene-Lewis acid complex;
   (iii) reacting said 1,4-bis(4-phenoxybenzoyl)benzene-Lewis acid complex with at least one difunctional aromatic acyl chloride in a reaction solvent and optional additional Lewis acid to obtain a product mixture comprising a PEKK-Lewis acid complex; and
   (iv) decomplexing the PEKK-Lewis acid complex to obtain a PEKK polymer.
2. The method of claim 1, wherein step (i) comprises:
(a) providing a reactant mixture comprising terephthaloyl chloride and diphenyl ether in a reaction solvent;
   (b) adding a Lewis acid to the reactant mixture, so as to obtain a product mixture comprising 1,4-bis(4-phenoxybenzoyl)benzene-Lewis acid complex.
3. The method of claim 1, wherein the 1,4-bis(4-phenoxybenzoyl)benzene-Lewis acid complex is purified using ortho-dichlorobenzene.
4. The method of claim 1, wherein the ortho-dichlorobenzene is recycled ortho-dichlorobenzene.
5. The method of claim 1, wherein step (iv) comprises:
   (a) contacting the obtained product mixture with a protic solvent so as to decomplex the PEKK-Lewis acid complex, whereby a dispersion is obtained that comprises a liquid phase comprising Lewis acid and a solid phase comprising PEKK; and
   (b) separating the solid phase of the dispersion from the liquid phase, so as to recover a crude PEKK and an effluent containing Lewis acid.
6. The method of claim 5, wherein the effluent containing Lewis acid is recycled.
7. The method of claim 1, wherein the at least one difunctional aromatic acyl chloride is selected from the group consisting of terephtaloyl chloride, isophtaloyl chloride, and mixtures thereof.
8. The method of claim 2, wherein the reaction solvent in step (ia) and step (iii) is ortho-dichlorobenzene, respectively.
9. The method of claim 1, wherein the Lewis acid is aluminum trichloride.
10. The method of claim 5, wherein the protic solvent in step (iva) is an aqueous solution.
11. The method of claim 1, further comprising after step (iv) one or more steps of washing the crude PEKK in a protic solvent, and subjecting the resulting mixture to a further solid/liquid separation.
12. The method of claim 1, further comprising after step (iv) one or more steps of washing the crude PEKK with a protic solvent, and subjecting the resulting mixture to a further solid/liquid separation.
13. The method of claim 1, wherein step (iv) and each subsequent washing step is performed in a centrifugal filtration device, without removing the PEKK between subsequent steps.
14. The method of claim 1, further comprising a subsequent step of drying the PEKK.
15. The method of claim 5, wherein the protic solvent in step (iva) is an aqueous solution, which has a pH of not more than 5.
16. The method of claim 1, further comprising after step (iv) one or more steps of washing the crude PEKK in methanol, and subjecting the resulting mixture to a further solid/liquid separation.
17. The method of claim 1, further comprising after step (iv) one or more steps of washing the crude PEKK with water, and subjecting the resulting mixture to a further solid/liquid separation.

* * * * *